(12) United States Patent
Ilan et al.

(10) Patent No.: US 8,677,935 B1
(45) Date of Patent: Mar. 25, 2014

(54) SYSTEM AND METHOD FOR PRODUCING BENEFICIAL PARASITES

(75) Inventors: David Shapiro Ilan, Macon, GA (US); W. Louis Tedders, Perry, CA (US); Juan A. Morales Ramos, Greenville, MS (US); Maria G. Rojas, Greenville, MS (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 264 days.

(21) Appl. No.: 13/217,956

(22) Filed: Aug. 25, 2011

(51) Int. Cl.
    *A01K 67/033* (2006.01)
(52) U.S. Cl.
    USPC .......................................................... 119/6.7
(58) Field of Classification Search
    USPC .................................. 119/6.5–6.7, 270, 174
    See application file for complete search history.

(56) References Cited

U.S. PATENT DOCUMENTS

| | | | |
|---|---|---|---|
| 3,468,289 A * | 9/1969 | Broida | 119/6.5 |
| 3,566,836 A * | 3/1971 | Elfert | 119/6.7 |
| 4,334,498 A * | 6/1982 | Bedding | 119/6.7 |
| 4,765,275 A * | 8/1988 | Yukawa et al. | 119/6.7 |
| 5,042,427 A * | 8/1991 | Bedding | 119/6.7 |
| 5,172,514 A * | 12/1992 | Weber et al. | 43/132.1 |
| 5,183,950 A * | 2/1993 | Popiel et al. | 800/8 |
| 5,466,448 A * | 11/1995 | Smart et al. | 424/93.1 |
| 6,474,259 B1 | 11/2002 | Gaugler | |
| 2003/0010293 A1* | 1/2003 | Gaugler et al. | 119/6.7 |

OTHER PUBLICATIONS

Gaugler, Randy et al., Automated Technology for in vivo mass production of entomopathogenic nematodes, Biological Control 24 (2002) 199-206.

Shapiro, David I. et al., Comparison of Entomopathogenic Nematode Infectivity from Infected Hosts Versus Aqueous Suspension, Environ. Entomol. 28 (5): 907-911 (1999).

* cited by examiner

*Primary Examiner* — Rob Swiatek
*Assistant Examiner* — Ebony Evans
(74) *Attorney, Agent, or Firm* — John Fado; Robert D. Jones; Lesley Shaw

(57) ABSTRACT

The system produces beneficial parasites by depositing parasite-infected cadavers adjacent to a filtering device inside an enclosed package. The parasites are then allowed to migrate from the infected cadavers, through the filtering device, and into a parasite-sustaining medium. After the migration is complete, the spent cadavers and the filtering device are removed and the package is closed. In the preferred embodiment, beneficial nematodes migrate through a screen matrix into polyacrylamide gel to create a package of beneficial nematodes.

18 Claims, 1 Drawing Sheet

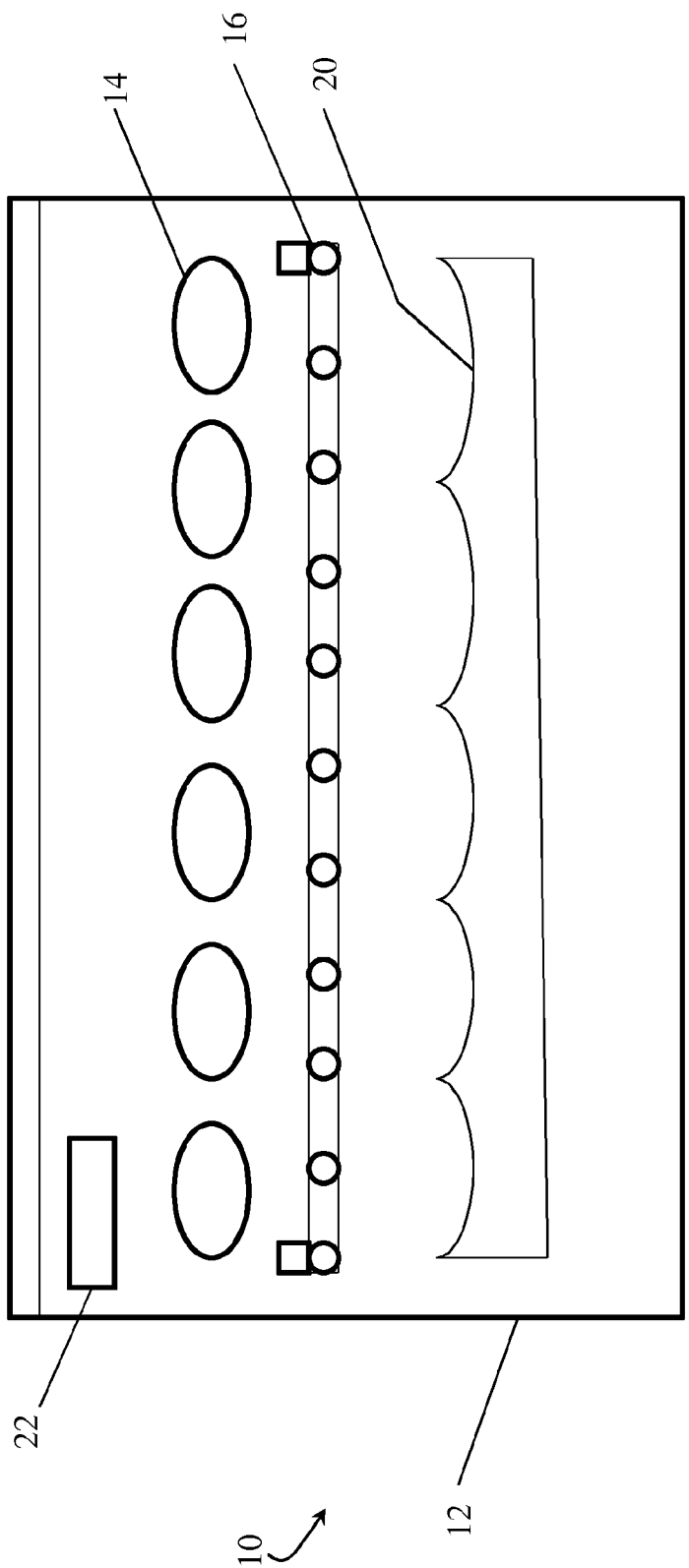

SYSTEM AND METHOD FOR PRODUCING BENEFICIAL PARASITES

FIELD OF THE INVENTION

The present invention relates to a system and method for producing beneficial parasites. Specifically, the invention relates to a system and method for producing beneficial nematodes.

BACKGROUND OF THE INVENTION

For multiple reasons, farmers are seeking biologically-based pest control alternatives to commercial synthetic chemical pesticides. One "biocontrol" strategy is to increase the presence of the insects' natural enemies. These natural enemies may include beneficial entomopathogenic nematodes such as *Steinernema* spp or *Heterorhabditis* spp. These beneficial nematodes are parasites that prey on a variety of damaging insects but pose no danger to plants or humans.

Commercial production of beneficial nematodes can be in vitro (e.g., in fermentation tanks), or in vivo using susceptible insect hosts. Although both production systems have advantages, in vivo systems generally result in the production of better quality and more virulent nematodes. Further, more nematode species can be produced in vivo, and in vivo production methods do not require the use of expensive and complex equipment.

The current process for in vivo production and packaging of nematodes is based on the "White trap" method in which nematodes are collected in a solution, the solution is strained, and then the nematodes are concentrated and deposited into a package for shipment. While this method is generally effective, it is also relatively labor intensive, and manipulation of the nematodes causes damage and stress to the nematodes and generally results in a less-than-optimal nematode product.

The need exists for a nematode production system and process that requires minimal labor and produces superior quality nematodes. The process and system of the current invention is simple and efficient and produces virulent nematodes that have not been stressed or damaged.

SUMMARY OF THE INVENTION

The current invention is directed to a parasite production system comprising, at least one nematode-infected cadaver, a filtering device, and a parasite-sustaining medium. The system is structured so that as a parasite emerges from the infected cadaver, the parasite migrates through the filtering device and into the parasite-sustaining medium.

The current invention is also directed to a method of producing a package of parasites. A filtering device is provided inside an open package and parasite-infected cadavers are placed adjacent to a first side of the filtering device, and parasite-sustaining medium is placed adjacent to a second side of the filtering device. Parasites are allowed to migrate from the cadavers, through the filtering device, and into the parasite-sustaining medium. The cadavers and the filtering device are then removed and the package is closed to produce the package of parasites.

In the preferred embodiment, the system and process of the current invention are used to produce a package of beneficial nematodes. In accordance with the current invention, beneficial nematodes (within a sealable ventilated plastic bag) migrate from infected mealworm cadavers through a screen matrix, and into polyacrylamide gel. The cadavers and the screen are removed from the bag and then the bag is sealed to create a package of beneficial nematodes.

BRIEF DESCRIPTION OF THE DRAWINGS

FIG. 1 is a sectional schematic of the current invention.

DETAILED DESCRIPTION OF PREFERRED EMBODIMENTS

As generally shown in FIG. 1, the present invention comprises a system 10 for producing beneficial parasites. The system 10 comprises an outer packaging 12 which encloses the system's other components. The system 10 further comprises a plurality of host cadavers 14 that have been infected by beneficial parasites. Although multiple host cadavers 14 are disclosed in FIG. 1, for the sake of simplicity, only one reference number is shown.

The host cadavers 14 are positioned on a restrictive filtering device 16 over a parasite-sustaining medium 20. As the parasites begin to emerge from the cadavers 14, the parasites migrate from the cadavers 14, through the filtering device 16, and into the medium 20, which sustains the parasites. A breathable patch 22 may be placed on the packaging 12 either before, during, or after the parasites emerge to ensure adequate ventilation. If the patch 22 is left in place after the parasites emerge, it should be constructed (or placed) to prevent the inadvertent escape of any of the parasites. Once essentially all of the parasites have emerged from the host cadavers 14, the filtering device 16 and the cadavers 14 are (generally) removed from the packaging 12 and the packaging 12 is closed and prepared for shipping.

In the preferred embodiment, the cadavers 14 comprise mealworm larvae (*Tenebrio molitor*) and the parasites are nematodes (typically *Steinernema* spp or *Heterorhabditis* spp). The packaging 12 is designed so that approximately one hundred host cadavers 14 are enclosed in each package 12. In the preferred embodiment, five million nematodes are produced in each package. In alternative embodiments, other types of cadavers may be used to produce different types of nematodes or beneficial parasites. The packaging 12 may also be larger or smaller than the preferred embodiment to accommodate various production requirements. In the preferred embodiment, the package 12 comprises a sealable plastic bag, however other constructions should be considered within the scope of the invention.

The nematodes typically begin to emerge approximately ten days after the cadavers 14 are infected. The filtering device 16 comprises a polyester screen with a mesh size of approximately 1×2 mm so that the nematodes emerge from the mealworm cadavers 14 and migrate through the screen 16 and into the parasite sustaining medium 20. As shown in FIG. 1, the screen 16 may include a small vertical lip to ensure that the cadavers remain within the circumference of the screen 16.

A breathable patch 22 is added to the plastic bag packaging 12 to ensure that the packaging is properly ventilated. In the preferred embodiment, the patch is comprised of TYVEK material (manufactured by the DuPont™ corporation), although other breathable materials should be considered within the scope of the invention. In alternative embodiments, an air tube (such as a filtered or unfiltered straw-type tube) may be used.

The parasite-sustaining medium 20 of the preferred embodiment comprises a long term sustaining medium. For the purposes of this invention, a long term parasite sustaining medium comprises a medium that enables a parasite to live for at least two weeks. The packaged nematodes are generally stored under refrigerated conditions at 4 to 13° C.

In the preferred embodiment, the parasite sustaining medium 20 comprises polyacrylamide gel. A typical package of comprises about 1 gram of polyacrylamide gel with 75 ml of water added for saturation. The unique properties of polyacrylamide crystals allow more oxygen to remain in solution thereby significantly enhancing the amount of time that the nematodes can remain viable. In the polyacrylamide gel 20, the produced nematodes can remain viable for more than six months.

During the nematode production process, the infected cadavers 14 exude substances that fall into polyacrylamide gel 20 and these exudates remain in the gel 20 after the screen 16 and the cadavers 14 are removed. The inventors have found that these exudates further enhance the virulence and viability of the produced nematodes. However, if the entire cadavers 14 are allowed to remain in the gel, the decomposing cadavers promote the growth of bacteria that may be harmful to the nematodes.

Once the packaged nematodes reach a target site, application of the polyacrylamide gel 20 to target plants prolongs a humid micro-climate that further sustains the nematodes and may also have other advantages. However, once the packaged nematodes reach the target site they can also be removed from the package (and the polyacrylamide gel) and distributed by any means known in the art.

For the foregoing reasons, it is clear that the invention provides an innovative system and method for producing beneficial nematodes. The invention may be modified in multiple ways and applied in various technological applications. For example, the current invention may be used to produce other organisms wherein the emergence of the organism from a host cadaver is a part of the organism's reproduction process.

The current invention may be modified and customized as required by a specific operation or application, and the individual components may be modified and defined, as required, to achieve the desired result. Although the materials of construction are generally not described, they may include a variety of compositions consistent with the function of the invention. Such variations are not to be regarded as a departure from the spirit and scope of the invention, and all such modifications as would be obvious to one skilled in the art are intended to be included within the scope of the following claims.

What is claimed is:

1. A parasite production system comprising:

at least one infected cadaver;

a filtering device;

a parasite-sustaining medium; and a ventilated bag, the at least one infected cadaver, the filtering device, and the parasite-sustaining medium being positioned in the bag;

wherein the system is structured so that as at least one parasite emerges from the at least one infected cadaver, the at least one parasite migrates through the filtering device and into the parasite-sustaining medium, the bag being essentially closed after the at least one parasite migrates to the parasite-sustaining medium so that the closed bag comprises a package.

2. The system of claim 1 wherein the filtering device comprises a screen.

3. The system of claim 1 wherein the at least one parasite comprises a nematode.

4. The system of claim 3 wherein the nematode comprises one of a *Steinernema* spp or *Heterorhabditis* spp.

5. The system of claim 3 wherein the at least one infected cadaver comprises at least one infected mealworm cadaver.

6. The system of claim 1 wherein the parasite-sustaining medium comprises a long term sustaining medium.

7. The system of claim 1 wherein the parasite-sustaining medium comprises a gel.

8. The system of claim 1 wherein the parasite-sustaining medium comprises polyacrylamide gel.

9. The system of claim 1 wherein the parasite-sustaining medium further comprises exudates from the at least one infected cadaver.

10. The system of claim 1 wherein the system is ventilated until the at least one parasite has essentially completed migration into the parasite-sustaining medium.

11. A method of producing a package of parasites comprising:

providing the system of claim 1;

after the parasites have migrated into the parasite-sustaining medium, removing the at least one infected cadaver and the filtering device.

12. The method of claim 11 wherein the filtering device is a screen.

13. The method of claim 11 wherein the parasite-sustaining medium is polyacrylamide gel.

14. A method of producing a package of parasites comprising the steps of:

(a) providing a filtering device inside an open package;

(b) placing parasite-infected cadavers adjacent a first side of the filtering device;

(c) positioning a parasite-sustaining medium adjacent a second side of the filtering device;

(d) allowing the parasites to migrate from the cadavers through the filtering device and into the parasite-sustaining medium;

(e) removing the cadavers and the filtering device; and (f) closing the open package to produce a closed package of parasites that are ready for use.

15. The method of claim 14 wherein the open package comprises a plastic bag.

16. The method of claim 14 wherein the filtering device is a screen.

17. The method of claim 14 wherein the parasite-sustaining medium is polyacrylamide gel.

18. The method of claim 17 wherein the polyacrylamide gel includes exudates from the parasite-infected cadavers.

* * * * *